(12) United States Patent
Raines

(10) Patent No.: US 11,571,572 B2
(45) Date of Patent: Feb. 7, 2023

(54) IMPLANTABLE PERIPHERAL NERVE STIMULATION LEAD

(71) Applicant: Advanced Neuromodulation Systems, Inc., Plano, TX (US)

(72) Inventor: Aaron Raines, Dallas, TX (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 1 day.

(21) Appl. No.: 17/227,185

(22) Filed: Apr. 9, 2021

(65) Prior Publication Data
US 2022/0184393 A1 Jun. 16, 2022

Related U.S. Application Data

(60) Provisional application No. 63/125,922, filed on Dec. 15, 2020.

(51) Int. Cl.
  *A61N 1/05* (2006.01)
  *A61N 1/36* (2006.01)
  *A61N 1/375* (2006.01)

(52) U.S. Cl.
  CPC ......... *A61N 1/3606* (2013.01); *A61N 1/0558* (2013.01); *A61N 1/37518* (2017.08); *A61N 1/36071* (2013.01)

(58) Field of Classification Search
  CPC .............. A61N 1/3606; A61N 1/0558; A61N 1/37518; A61N 1/36071
  See application file for complete search history.

(56) References Cited

U.S. PATENT DOCUMENTS

| | | | |
|---|---|---|---|
| 4,541,440 A | 9/1985 | Parsonnet | |
| 5,374,285 A * | 12/1994 | Vaiani | A61N 1/0551 29/850 |
| 5,562,723 A | 10/1996 | Rugland et al. | |
| 7,912,555 B2 * | 3/2011 | Swoyer | A61N 1/0558 607/116 |

(Continued)

OTHER PUBLICATIONS

Patent Cooperation Treaty, International Search Report and Written Opinion issued for PCT Application No. PCT/US2021/063172, dated Mar. 3, 2022, 12 pages.

(Continued)

*Primary Examiner* — Eugene T Wu
(74) *Attorney, Agent, or Firm* — Norton Rose Fulbright US LLP

(57) ABSTRACT

The present disclosure provides a stimulation lead for providing stimulation signals to nerve tissue and improved methods for constructing and manufacturing such a stimulation lead. The stimulation lead and/or methods includes a lead with a cable disposed within. At each end of the lead body a portion of the cable is exposed, and a metal ferrule is securely attached to the exposed cable portion. An electrode/contact is then securely attached to the metal ferrule such that the electrode covers the metal ferrule, a portion of the lead body, and a transition point where the exposed cable exits the lead body. A tine component may be swaged around a portion of the term end, configured to provide a retaining force against an force acting upon the stimulation lead, while allowing insertion of the stim end of the stimulation lead during implantation, and extraction of the stim end during explantation.

29 Claims, 8 Drawing Sheets

(56) References Cited

U.S. PATENT DOCUMENTS

| | | | |
|---|---|---|---|
| 8,523,588 B2 * | 9/2013 | Forslund | H01R 24/58 439/668 |
| 2013/0150808 A1 | 6/2013 | Ogle et al. | |
| 2016/0045724 A1 | 2/2016 | Lee et al. | |

OTHER PUBLICATIONS

Perryman, L.T., "Peripheral Nerve Stimulation and Percutaneous Electrical Nerve STimulation in Pain Management: A Review and Update on Current Status," International Journal of Pain & Relief, 2017, vol. 1, No. 1, pp. 036-041.

* cited by examiner

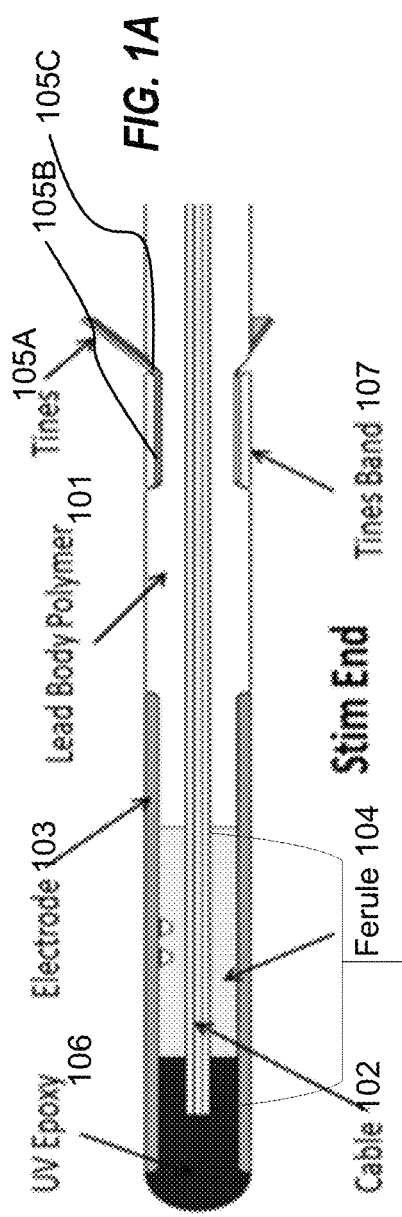
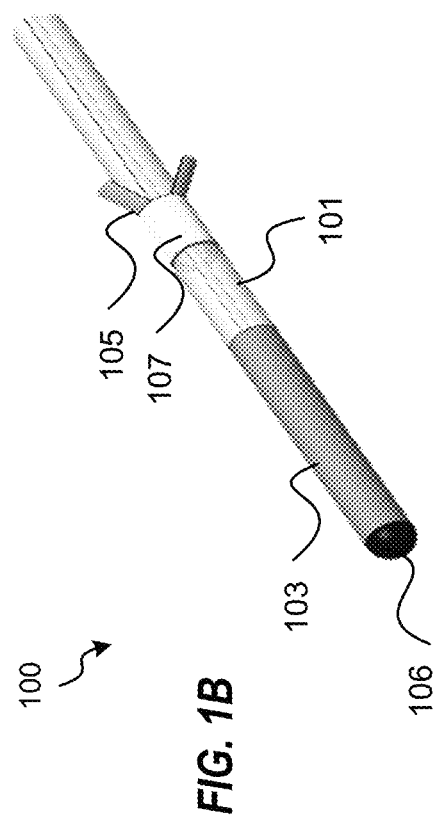

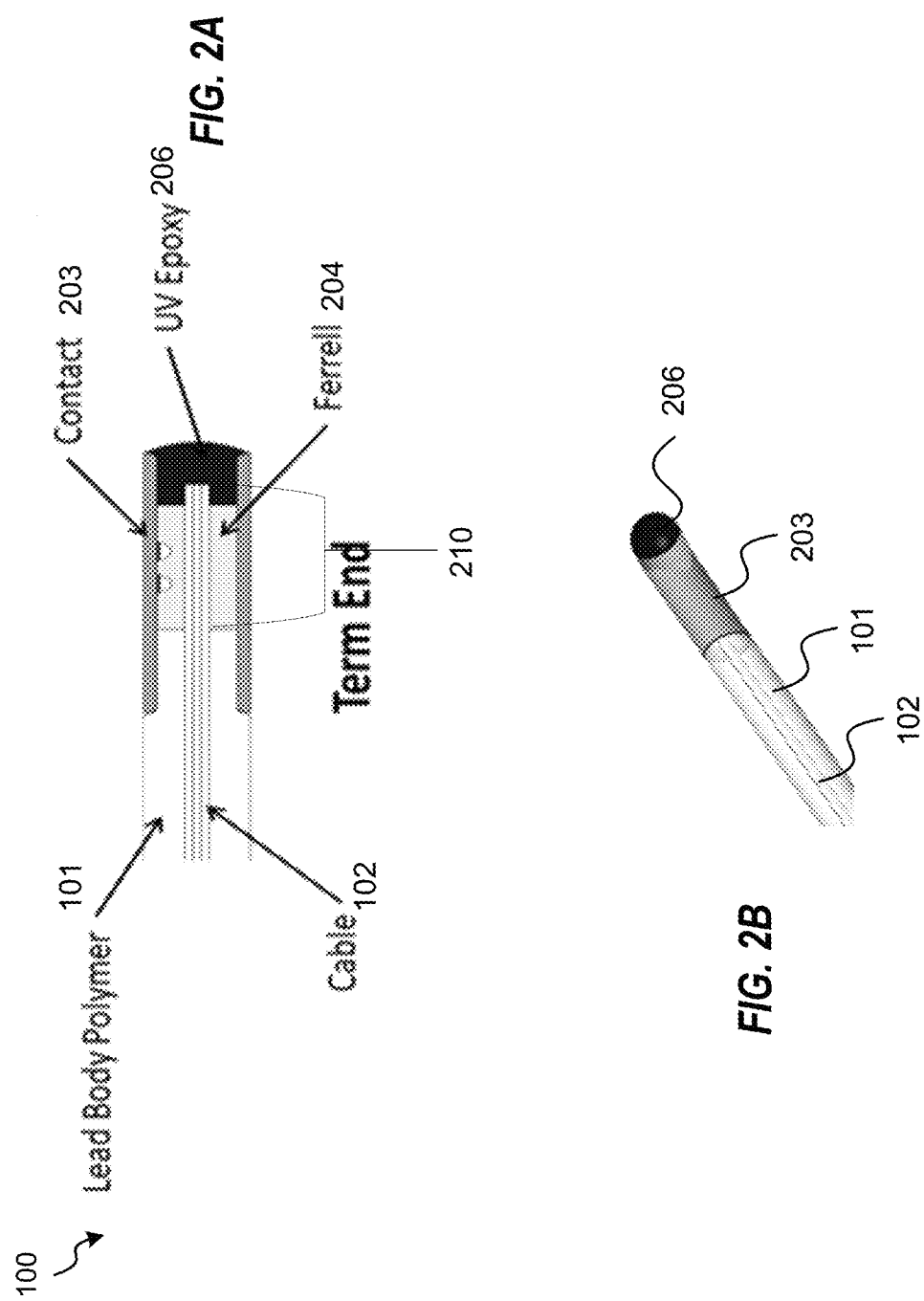

IMPLANTABLE PERIPHERAL NERVE STIMULATION LEAD

CROSS-REFERENCE TO RELATED APPLICATION

The present application claims the benefit of U.S. Provisional Patent Application No. 63/125,922 filed Dec. 15, 2020, and entitled "IMPLANTABLE PERIPHERAL NERVE STIMULATION LEAD," the disclosure of which is incorporated by reference herein in its entirety.

TECHNICAL FIELD

The present disclosure relates generally to medical devices, and more particularly to a peripheral nerve stimulation lead.

BACKGROUND

Nerve stimulation has been shown to be helpful in treating patients with chronic intractable pain. For those patients who prove unresponsive to conservative pain management techniques, peripheral nerve stimulation (PNS) may be a successful therapy for pain management when the pain is known to result from a specific nerve. PNS is based in part on the Melzack-Wall gate control theory of pain. Sweet and Wespic first used electrical stimulation of peripheral nerves in the 1960s to mask the sensation of pain with a tingling sensation (paresthesia) caused by the electrical stimulation. Subsequent refinements in the technology, surgical techniques and patient selection have led to improved long term results.

PNS typically involves a procedure in which an electrode of a stimulation lead is placed adjacent to one of the peripheral nerves. Peripheral nerves are the nerves that are located beyond the brain or spinal cord. The electrode delivers electrical pulses generated by an external or implanted device (e.g., a stimulation generator or a pulse generator) to the nerve tissue. In some current implementations, the stimulation lead is implanted within the patient, such that the electrode is placed adjacent to the target nerve tissue. However, the size of current implantable stimulation leads is not ideal for implantable solutions. In addition, current implantable stimulation leads are constructed using techniques, such as welding wires and cables on the inside of the electrode, which render them more difficult to manufacture and more expensive.

BRIEF SUMMARY OF THE INVENTION

Aspects of the present invention are directed to a stimulation lead for providing stimulation signals to a target nerve and to improved techniques for constructing and manufacturing such a stimulation lead. In aspects, the stimulation lead of embodiment may be implantable and may be used in PNS applications. The stimulation lead of embodiments includes a lead body having a proximal end, also referred to herein as a term end, configured to connect to a stimulation signal generator, and a distal end, also referred to herein as a stim end, configured to be implanted within a patient and positioned adjacent to a target nerve. The stimulation lead of embodiments may include a lead body with a cable disposed within the lead body, and with a portion of the cable exposed at, or extending out of, each end of the lead body (e.g., the proximal end and the distal end). A metal ferrule may be securely attached (e.g., crimped) around the distal portion of the cable that extends out of the distal end of the lead body and around the proximal portion of the cable that extends out of the proximal end of the lead body. An electrode may be securely attached (e.g., swaged) around the distal metal ferrule and a portion of the distal end of the lead body such that the electrode surrounds a transition point at which the exposed cable exits the lead body at the distal end of the stimulation lead. In some embodiments, a contact may be securely attached (e.g., swaged) around the proximal metal ferrule and a portion of the proximal end of the lead body such that the contact surrounds a transition point of the cable to the lead body (e.g., the point at which the exposed cable exits the lead body) at the proximal end of the stimulation lead.

In some embodiments, a tine component may be securely attached (e.g., swaged) around a portion of the distal end of the lead body. The tine component may be configured to provide a retaining force against a force exerted in an extraction direction acting upon the stimulation lead, while allowing insertion of the stim end of the stimulation lead during implantation, and extraction of the stim end during explantation. For example, the tine component may include a plurality of tine features, also referred to herein as tines, that may be configured to fold down onto the lead body during insertion of the stimulation lead thereby allowing the stim end of the stimulation lead, including the electrode, to be inserted into the patient. The tine features of the stimulation lead may also be configured to remain folded at an anchoring angle away from the stim end of the stimulation lead. This configuration of the tine features provides a retaining force against the force exerted in the extraction direction, and maintains the stimulation lead anchored within the patient. In aspects, the tine features may be configured to fold up and back down against the lead body in the direction of the stim end when the force exerted is an extraction force of sufficient amount applied against the stimulation lead, thereby allowing the stim end to be extracted from the patient. As such, in aspects, when the force exerted in the extraction direction upon the stim end of the stimulation lead does not exceed the threshold, the tine features may remain in the anchor position and the retaining force may hold, thereby preventing the stim end from being displaced in the direction of extraction and/or extracted from the patient. In this manner, the tine component is configured to anchor the stim end within the patient to prevent accidental displacement of the lead in the direction of the force exerted in the extraction direction and/or extraction of the stimulation lead when the stimulation lead is tugged on or pulled during use. However, when the force exerted in the extraction direction exceeds the threshold, the tine features may not remain in the anchor position and may instead fold up and then down in the direction of the stim end, and the retaining force may yield, thereby allowing the stim end to be extracted from the patient. In this manner, the tine component is configured to allow the stim to be removed or extracted from the patient with minimal or no damage.

In aspects of the present disclosure, the stimulation lead of embodiments may be manufactured using crimping and swaging techniques, instead of the more traditional welding techniques of current stimulation leads. For example, in some embodiments, a lead body of the stimulation lead may be stripped off to expose a portion of the cable disposed within the lead body. A metal ferrule may then be crimped onto the exposed portion of the cable, and an electrode or contact may be swaged over the metal ferrule. The same operations may be performed on both the distal end and the proximal end of the lead body. As noted above, these crimping and swaging techniques simplify the manufacturing of the stimulation lead of embodiments and reduce costs.

In some embodiments, the electrode or contact may be swaged onto the metal ferrule in such a manner that the electrode also covers at least a portion of the lead body. For example, the electrode may be swaged such that it also covers or surrounds a transition point of the cable to the lead body (e.g., the point at which the exposed cable exits the lead body). These techniques provide a strain relief to the stimulation lead, e.g., by eliminating or reducing the stress on the transition point due to a bending force, which is a high fatigue area, and prone to failure, as it is the point at which the cable exits the lead body.

In some embodiments, a tine component may be swaged onto the stim end of the stimulation lead and may be configured to provide a retaining force against a force exerted in the extraction direction upon the stimulation lead, while allowing insertion of the stim end of the stimulation lead during implantation, and extraction of the stim end during explantation. In embodiments, the tine component may be constructed by fabricating (e.g., die-cutting, forming, 3D printing, mold injecting, etc.) a tine sheet from a highly flexible polymer sheet. In embodiments, the tine sheet may include a band portion and a plurality of tines disposed around the band portion. The tine sheet may be rolled into a cylindrical shape such that the band portion forms a cylindrical band with the tine features disposed around the band. The cylindrical tine sheet may then be inserted into a metal band, and the metal band may then be swaged onto the stim end of the stimulation lead.

Other aspects, features, and implementations will become apparent to those of ordinary skill in the art, upon reviewing the following description of specific, exemplary aspects in conjunction with the accompanying figures. While features may be discussed relative to certain aspects and figures below, various aspects may include one or more of the advantageous features discussed herein. In other words, while one or more aspects may be discussed as having certain advantageous features, one or more of such features may also be used in accordance with the various aspects. In similar fashion, while exemplary aspects may be discussed below as device, system, or method aspects, the exemplary aspects may be implemented in various devices, systems, and methods.

BRIEF DESCRIPTION OF THE DRAWINGS

A further understanding of the nature and advantages of the present disclosure may be realized by reference to the following drawings. In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

FIG. 1A illustrates an example cross-sectional view of a distal end of a stimulation lead configured in accordance with aspects of the present disclosure.

FIG. 1B shows a perspective view of an example of a distal end of a stimulation lead configured in accordance with aspects of the present disclosure.

FIG. 2A illustrates an example cross-sectional view of a proximal end of a stimulation lead configured in accordance with aspects of the present disclosure.

FIG. 2B shows a perspective view of an example of a proximal end of a stimulation lead configured in accordance with aspects of the present disclosure.

Figure 3:
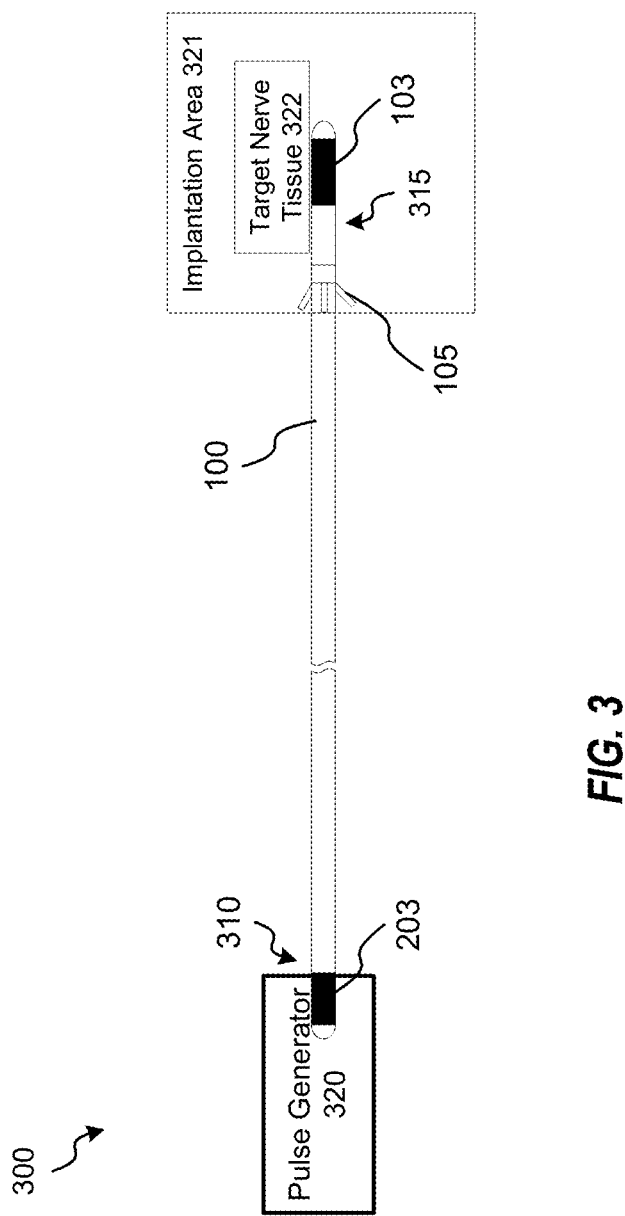
FIG. 3 shows an example of a system for nerve stimulation during operations using a stimulation lead implemented in accordance with aspects of the present disclosure.

It should be understood that the drawings are not necessarily to scale and that the disclosed aspects are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular aspects illustrated herein

DETAILED DESCRIPTION OF THE INVENTION

Unless defined otherwise, technical and scientific terms used herein have the same meaning as commonly understood by one of ordinary skill in the art to which this invention belongs. For purposes of the present invention, the following terms are defined below.

As used herein, the use of the word "a" or "an" when used in conjunction with the term "comprising" in the claims and/or the specification may mean "one," but it is also consistent with the meaning of "one or more", "at least one", and "one or more than one." Still further, the terms "having", "including", "containing" and "comprising" are interchangeable and one of skill in the art is cognizant that these terms are open ended terms.

As used herein, the term "peripheral nerve" refers a neuron or a bundle of neurons comprising a part of the peripheral nervous system. The nervous system comprises two general components, the central nervous system, which is composed of the brain and the spinal cord, and the peripheral nervous system, which is composed of ganglia or dorsal root ganglia and the peripheral nerves that lie outside the brain and the spinal cord. One of skill in the art realizes that the nervous system may be separated anatomically, but functionally they are interconnected and interactive. The peripheral nervous system is divided into the autonomic system (parasympathetic and sympathetic), the somatic system and the enteric system. The term peripheral nerve is intended to include both motor and sensory neurons and neuronal bundles of the autonomic system, the somatic system, and the enteric system that reside outside of the spinal cord and the brain. Peripheral nerve ganglia and nerves located outside of the brain and spinal cord are also described by the term peripheral nerve.

As used herein, the term "stimulate" or "stimulation" refers to electrical, chemical, and/or magnetic stimulation that modulates a predetermined site, such a location that includes target nerve tissue.

As used herein, the term "treating" and "treatment" refers to modulating certain areas of the brain so that the subject has an improvement in the disease, for example, beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. One of skill in the art realizes that a treatment may improve the disease condition, but may not be a complete cure for the disease.

As used herein, the term "crimping" may refer to a manufacturing technique in which a component is compressed against an item in order to form a bond between the component and the item. This crimping process joins the component to the item.

As used herein, the term "swaging" may refer to a manufacturing technique in which the dimensions of a component (e.g., a metal component) are changed using dies into which the component is forced. This process results in the cross section or diameter of the component being reduced. The reduction of the diameter of the component has the effect of pressing the component onto whichever item the component is swaged thereby joining or bonding the component to the item.

As noted above, nerve stimulation may be performed using stimulation leads to deliver stimulation signals to target nerve tissue. However, current stimulation leads are not ideally suited for PNS because of their large size, and have high cost due to the manufacturing process used to produced them. Aspects of the present invention are directed to an implantable stimulation lead that addresses the issues with current PNS leads, and to improved techniques for constructing and manufacturing such a stimulation lead.

FIG. 1A illustrates an example cross-sectional view of a distal end of a stimulation lead configured in accordance with aspects of the present disclosure. FIG. 1B shows a perspective view of the distal end of a stimulation lead configured in accordance with aspects of the present disclosure. In the example illustrated in FIGS. 1A and 1B, the stimulation lead is shown as stimulation lead 100. As shown in FIG. 1A, the distal end, or stim end, of stimulation lead 100 includes components that are configured and disposed to enable the stim end of stimulation lead 100 to be implanted within a patient to place an electrode adjacent to a target nerve (e.g., nerve tissue that is to be treated using stimulation signals), and to deliver stimulation signals to the tissue of the target nerve. In particular, stimulation lead 100 may include lead body 101. In some embodiments, lead body 101 may be constructed of insulative material, such as a polymer, and may function as the main structure of stimulation lead 100 to or upon which other components of stimulation lead 100 may be attached.

In embodiments, cable 102 may be disposed within lead body 101 (e.g., such as within a lumen defined longitudinally within the lead body) such that lead body 101 may surround, insulate, and/or protect cable 102. Cable 102 may include one or more conductors (e.g., insulated or uninsulated wire conductors) and may be configured to transmit electrical signals or pulses, which may be used as stimulation signals, from a stimulation signal generator to the stim end, and in particular electrode 103, of stimulation lead 100. Thus, in embodiments, cable 102 may extend from the proximal end of stimulation lead 100 to the distal end of stimulation lead 100. As noted above, the one or more conductors of cable 102 may electrically couple a contact on the term end of stimulation lead 100 (shown in FIG. 2A) to electrode 103 on the stim end of stimulation lead 100.

As shown in FIG. 1A, cable 102 may include, at the stim end of stimulation lead 100, cable portion 110 that extends beyond or outside of lead body 101. Cable portion 110 extends from the point at which cable portion 110 exits lead body 101 to the end point of cable 102 at the distal end of stimulation lead 100. In aspects, the point at which cable portion 110 exits lead body 101 may be referred to as a distal transition point, as this is the point at which the cable transitions from being outside lead body 101 to being within lead body 101. Traditionally, this distal transition point is a point of high fatigue and it is especially susceptible to mechanical failure (e.g., cable 102 may snap off at this point, or any number of the one or more conductors that may make up cable 102 may break off). Also, it is noted that cable portion 110 may also be referred to herein as the exposed portion of cable 102, as cable portion 110 is exposed with respect to lead body 101 in that cable portion 110 is not within lead body 101. In embodiments, cable portion 110 may be obtained by stripping off a portion of lead body 101 from stimulation lead 100 to expose cable 102. However, once the stim end of stimulation lead 100 is completed for use, cable portion 110 may no longer be exposed because cable portion 110 may be surrounded and covered by distal metal ferrule 104, electrode 103 and/or distal ultraviolet (UV) epoxy dome 106.

In embodiments, the stim end of stimulation lead 100 may also include distal metal ferrule 104. Distal metal ferrule 104 may be a ferrule configured to surround cable 102, and in particular to surround at least a portion of cable portion 110. Distal metal ferrule may be a cylindrical component, with a hollow channel through the center, through which the distal end of cable 102 may slide. In aspects, distal metal ferrule 104 may be configured to cover a portion from the distal transition point (e.g., the point at which cable 102 exits lead body 101 at the distal end of stimulation lead 100) to near the distal end point of cable 102. In aspects, distal metal ferrule 104 may be positioned over cable portion 110 such that one end of distal metal ferrule 104 is pressed against the distal transition point (e.g., the point at which cable 102 exits lead body 101).

Distal metal ferrule 104 may be electrically coupled to the cable. For example, distal metal ferrule 104 may be crimped, swaged, or otherwise joined to cable 102 in such a way as to cause distal metal ferrule 104 to be retained against cable 102 while maintaining an electrical connection (e.g., via physical contact) with one or more conductors thereof. In some embodiments, cable 102 may be include one or more insulated wire conductors. In this case, the insulation of the one or more insulated wire conductors may be removed or stripped off before distal metal ferrule 104 is attached to cable 102, thereby ensuring an electrical connection between distal metal ferrule 104 and cable 102. As such, a stimulation signal may be conducted or transmitted from the cable through distal metal ferrule 104 to electrode 103.

In embodiments, the stim end of stimulation lead 100 may also include electrode 103. Electrode 103 may be a cylindrical ring that slides over the stim end of stimulation lead 100 and surrounds distal metal ferrule 104 and a portion of the distal end of lead body 101 that includes the distal transition point. In some aspects, electrode 103 may cover a portion of the stim end that begins at a point on lead body 101 beyond the distal transition point, covers the distal transition point and distal metal ferrule 104, and ends at a point beyond the distal end of cable 102. In that manner, electrode 103 surrounds a portion of lead body 101, the distal transition point, distal metal ferrule 104, and the distal end of cable 102. In embodiments, electrode 103 may be securely attached to the stim end of stimulation lead 100, and in particular onto distal metal ferrule 104, in such a way as to cause electrode 103 to be retained against the stim end of stimulation lead 100, while maintaining an electrical connection (e.g., via physical contact) with distal metal ferrule 104. In embodiments, securely attaching electrode 103 to the stim end may include swaging, crimping, or otherwise joining electrode 103 to the stim end of stimulation lead 100. However, it is noted that swaging reduces the diameter of electrode 103, but may generally keep the original circular shape of electrode 103. As such, swaging electrode 103 onto the stim end of stimulation lead 100 may provide an effective "seal" over the stim end of stimulation lead 100. Crimping, however, may flatten or distort the shape of electrode 101, and would create irregularities in the shape of electrode 103 that may allow bodily fluids to enter the lumen of stimulation lead 100.

In aspects, electrode 103 may be constructed of a conductive material such as a metal, and may be electrically connected (e.g., via physical contact) to distal metal ferrule 104. Electrode 103, may be configured to receive stimulation signals from a stimulation signal generator, via cable 102 and distal metal ferrule 104, and to deliver the stimulation to the target nerve tissue. As such, a stimulation signal may be conducted or transmitted from the cable through distal metal ferrule to electrode 103, and delivered to the target nerve tissue, as electrode 103 is configured to be placed adjacent to the target nerve tissue. In some embodiments, electrode 103 may be configured to sense physiological signals from the patient.

In embodiments, electrode 103 may be configured to provide strain relief, or bend relief, to the stim end of stimulation lead 100. For example, as discussed above, electrode 103 is joined to the stim end of stimulation lead 100 and surrounds a portion of lead body 101, the distal transition point, and distal metal ferrule 104. As such, electrode 103 provides a resisting force against a bending force acting upon the distal transition point, which is the point at which stimulation lead transitions from lead body 101 to cable 102, and is a particularly vulnerable point for mechanical failure. In that case, the connection of electrode 103 to the portion of lead body 101 and the connection of electrode 103 to distal metal ferrule 104 serve as anchors that prevent the distal transition point from excessive bending.

In embodiments, the stim end of stimulation lead 100 may also include distal UV epoxy dome 106. In aspects, distal UV epoxy dome 106 may comprise an injectable epoxy that is reactive to UV light and cures upon the application of UV light. In embodiments, the UV epoxy may be injected into the distal end of stimulation lead 100, and the distal end may be exposed to a UV light. The UV light may cause the UV epoxy to begin curing. In embodiments, distal UV epoxy dome 106 may be placed at the end of the stim end of stimulation lead 100, and may function to secure and/or protect, the end points of electrode 103, cable 102, and distal metal ferrule 104. For example, distal UV epoxy dome 106 may function to seal the distal end of stimulation lead 100 and prevent bodily fluids from infiltrating the distal end. It is noted that the description of a UV epoxy dome is for illustrative purposes and not by way of limitation. In some embodiments, a non-UV epoxy may be used to provide an epoxy dome with functionality that is similar to distal UV epoxy dome 106. Thus, the use of a UV epoxy should not be construed as limiting in any way.

In embodiments, the stim end of stimulation lead 100 may also include tine component 105. Tine component 105 may include band portion 105B and a plurality of tines 105A, also referred to herein as tine features, disposed around band portion 105B. In embodiments, tine component 105 may be attached to stimulation lead 100 by band 107. Band 107 may be swaged or crimped onto stimulation lead 100, while positioned (e.g., by sliding band 107 over the tine component 105 when tine component is appropriately disposed in the distal end of lead body 101) over band portion 105B. In this manner, band 107 may secure and attach tine component 105 onto stimulation lead 100. In embodiments, the tine component may be constructed by fabricating (e.g., die-cutting, forming, 3D printing, mold injecting, etc.) a tine sheet from a highly flexible polymer sheet. The tine sheet, which may include band portion 105B and a plurality of tines 105A disposed around band portion 105B may be rolled into a cylindrical shape such that the band portion forms a cylindrical band with tines 105A disposed around band 105B. In embodiments, the tine sheet may be sufficiently flexible to allow the plurality of tines 105A to hinge (e.g., at folding point 105C) with respect to band portion 105B, while also being sufficiently rigid to allow the plurality of tines 105A to hold a shape and angle in order to prevent unwanted displacement or movement of the stim end. For example, in some embodiments, the tine sheet may have a grain or orientation of fibers, which may provide more rigidity in the direction of the grain. In embodiments, the tine sheet may be fabricated by cutting or forming plurality of tines 105A so that the tines are disposed along the grain and band portion may be rolled at a 90 degree angle off the grain orientation.

Tine component 105 may be configured to provide a retaining force against a force exerted in the extraction direction upon stimulation lead 100, while facilitating implantation of stimulation lead 100 onto a patient. For example, as shown in FIG. 1A, each tine 105A may be folded at folding point 105C at an anchoring angle which positions each tine to point away from the stim end of stimulation lead 100. In embodiments, tine component 105 may be initially formed with each tine of the plurality of tines 105A in an anchor position (e.g., having the anchoring angle), and the memory of the tine component material may provide a bias that causes the tines to return to or toward the anchoring position if the tines are deflected.

In embodiments, the anchoring angle of tines 105A facilitates insertion of the stim end of stimulation lead 100 during implantation. For example, when an insertion force is applied against tines 105A, in a direction away from the distal end of stimulation lead 100, tines 105A may fold down onto lead body 101 thereby allowing the stim end of stimulation lead 100 to be inserted into a patient.

In embodiments, the anchoring angle of tines 105A is such that a force exerted in the extraction direction applied on stimulation lead 100 may cause a resisting force to be applied against tines 105A in the direction of folding point 105C, which may oppose the folding of tines 105A due to the anchoring angle of tines 105A. If the force exerted in the extraction direction does not exceed a particular threshold, the resisting force may not be overcome and tines 105A may remain at the anchoring angle. For example, the force exerted in the extraction direction may be a pulling force acting upon stimulation lead 100 due to normal use. In this case, the retaining force caused by the configuration of tines 105A may prevent accidental displacement of the stim end stimulation lead 100 within the implantation area. However, when the force exerted in the extraction direction exceeds the threshold, the resisting force may be overcome and tines 105A may fold in the direction of the distal end of stimulation lead 100, and may fold down onto lead body 101 thereby allowing stimulation lead 100 to be removed. For example, the force exerted in the extraction direction may be an extraction force acting upon stimulation lead 100 to remove stimulation lead 100 from the patient. In this case, the extraction force may be sufficient to overcome the resistance of tines 105A thereby allowing extraction of stimulation lead 100. The particular functionality of tine component 105 is discussed in more detail with respect to FIG. 4.

FIG. 2A illustrates across-sectional view of an example of a proximal end of a stimulation lead (e.g., stimulation lead 100) configured in accordance with aspects of the present disclosure. FIG. 2B shows a perspective view of the proximal end of a stimulation lead configured in accordance with aspects of the present disclosure. As shown in FIGS. 2A and 2B, the proximal end, or term end, of stimulation lead 100 includes components that are configured and disposed to enable the term end of stimulation lead 100 to be connected to a stimulation signal generator. Stimulation signals may be provided by the stimulation signal generator to the term end of stimulation lead 100 via contact 203, passed through proximal metal ferrule 204 to cable 102 and carried to the stim end of stimulation lead 100 by cable 102. As discussed above, the stim end of stimulation lead 100 may be configured to deliver the stimulation signals to the target nerve tissue.

In embodiments, the term end of stimulation lead 100 may include the proximal end of lead body 101 and cable 102 disposed within lead body 101 (e.g., such as within a lumen defined longitudinally within lead body 101). As shown in FIG. 2A, cable 102 may include, at the term end of stimulation lead 100, cable portion 210 that extends beyond or outside of lead body 101. Cable portion 210 extends from the point at which cable 102 exits lead body 101 to the end point of cable 102 at the proximal end of stimulation lead 100. In aspects, the point at which cable portion 210 exits lead body 101 may be referred to as a proximal transition point, as this is the point at which cable 102 transitions from being outside lead body 101 to being within lead body 101 at the proximal end of lead body 101. As noted above, traditionally, this proximal transition point is a point of high fatigue and it is especially susceptible to mechanical failure (e.g., cable 102 may snap off at this point, or any number of the one or more conductors that may make up cable 102 may break off) as it may not have strain relief at this transition point. Also, it is noted that cable portion 210 may also be referred to herein as the exposed portion of cable 101, as described above with respect to cable portion 110 of FIG. 1A. In embodiments, cable portion 210 may be obtained by stripping off a portion of lead body 101 of stimulation lead 100 at the proximal end of stimulation lead 100 to expose cable 102. However, once the term end of stimulation lead 100 is completed for use, cable portion 210 may no longer be exposed because cable portion 210 may be surrounded and covered by proximal metal ferrule 204, contact 203 and/or proximal ultraviolet (UV) epoxy dome 206.

In embodiments, the proximal end of stimulation lead 100 may include proximal metal ferrule 204. Proximal metal ferrule 204 may be similar to distal metal ferrule 104 described above with respect to FIG. 1A. Proximal metal ferrule 204 may be a ferrule configured to surround cable 102, and in particular to surround at least a portion of cable portion 210. Proximal metal ferrule may be a cylindrical component, with a hollow channel through the center, through which the proximal end of cable 102 may slide. In aspects, proximal metal ferrule 204 may be configured to cover a portion from the proximal transition point (e.g., the point at which cable 102 exits lead body 101 at the proximal end of stimulation lead 100) to near the proximal end point of cable 102. In aspects, proximal metal ferrule 204 may be positioned over cable portion 210 such that one end of proximal metal ferrule 204 is pressed against the proximal transition point (e.g., the point at which cable 102 exits lead body 101).

Proximal metal ferrule 204 may be electrically coupled to cable 102. For example, proximal metal ferrule 204 may be crimped, swaged, or otherwise joined to cable 102 in such a way as to cause proximal metal ferrule 204 to be retained against cable 102 while maintaining an electrical connection (e.g., via physical contact) with one or more conductors thereof. In some embodiments, cable 102 may be include one or more insulated wire conductors. In this case, the insulation of the one or more insulated wire conductors may be removed or stripped off before proximal metal ferrule 204 is attached to cable 102, thereby ensuring an electrical connection between proximal metal ferrule 204 and cable 102. As such, a stimulation signal may be conducted or transmitted from a stimulation signal generator, via contact 203, through proximal metal ferrule 204 to cable 102.

In embodiments, the term end of stimulation lead 100 may include contact 203. Contact 203 may be a cylindrical ring that slides over the term end of stimulation lead 100 and surrounds proximal metal ferrule 204 and a portion of the proximal end of lead body 101 that includes the proximal transition point. In some aspects, contact 203 may cover a portion of the term end that begins at a point on lead body 101 beyond the proximal transition point, covers the proximal transition point and proximal metal ferrule 204, and ends at a point beyond the proximal end of cable 102. In that manner, contact 203 surrounds a portion of lead body 101, the proximal transition point, proximal metal ferrule 204, and the proximal end of cable 102. In embodiments, contact 203 may be crimped, swaged, or otherwise joined onto the term end of stimulation lead 100, and in particular onto proximal metal ferrule 204, in such a way as to cause contact 203 to be retained against the term end of stimulation lead 100, while maintaining an electrical connection (e.g., via physical contact) with proximal metal ferrule 204. It is noted that although contact 203 may be swaged or crimped onto the term end of stimulation lead 100, swaging, as discussed above, may provide a better seal than crimping.

In aspects, contact 203 may be constructed of a conductive material, such as a metal, and may be electrically connected (e.g., via physical contact) to proximal metal ferrule 204. Contact 203 may be configured to connect to a stimulation signal generator, and to receive stimulation signals from the stimulation signal generator. The stimulation signals may be transmitted through proximal metal ferrule 204 to cable 102, and then transmitted via cable 102 to the stim end of stimulation lead 100 for delivery to the target nerve.

In embodiments, contact 203 may be configured to provide strain relief, or bend relief, to the term end of stimulation lead 100. For example, as discussed above, contact 203 is joined to the term end of stimulation lead 100 and surrounds a portion of lead body 101, the proximal transition point, and proximal metal ferrule 204. As such, contact 203 provides a resisting force against a bending force acting upon the transition point, which is the point at which stimulation lead transitions from lead body 101 to cable 102, and is a particularly vulnerable point for mechanical failure.

In that case, the connection of contact 203 to the portion of lead body 101 and the connection of contact 203 to proximal metal ferrule 204 serve as anchors that prevent the proximal transition point from excessively bending and potentially failing.

In embodiments, the term end of stimulation lead 100 may also include proximal UV epoxy dome 206. In aspects, proximal UV epoxy dome 206 may comprise an injectable epoxy that is reactive to UV light and cures upon the application of UV light. In embodiments, the UV epoxy may be injected into the proximal end of stimulation lead 100, and the proximal end may be exposed to a UV light. The UV light may cause the UV epoxy to begin curing. In embodiments, proximal UV epoxy dome 206 may be placed at the end of the term end of stimulation lead 100, and may function to secure and/or protect, the end points of contact 203, cable 102, and proximal metal ferrule 104. For example, proximal UV epoxy dome 206 may function to seal the proximal end of stimulation lead 100 and prevent bodily fluids from infiltrating the proximal end. It is noted that the description of a UV epoxy dome is for illustrative purposes and not by way of limitation. In some embodiments, a non-UV epoxy may be used to provide an epoxy dome with functionality that is similar to proximal UV epoxy dome 206. Thus, the use of a UV epoxy should not be construed as limiting in any way.

FIG. 3 shows an example of a system for nerve stimulation during operations using a stimulation lead implemented in accordance with aspects of the present disclosure. The system illustrated in FIG. 3 is shown as system 300, and may include pulse generator 320 and stimulation lead 100. Stimulation lead 100 may be a stimulation lead configured in accordance with aspects of the present disclosure (e.g., stimulation lead 100 of FIGS. 1A and 2A), and may include stim end 315 and term end 310.

As shown in the example illustrated in FIG. 3, stim end 315 of stimulation lead 100 may be implanted into implantation area 321, and may be placed such that electrode 103 of stimulation lead 100 is placed adjacent to target nerve tissue 322. Stim end 315 may be configured and may include the same components as the stim end of stimulation lead 100 described with respect to FIG. 1A. Target nerve tissue 322 may be a nerve, nerves, or nerve tissue which is/are targeted for stimulation using stimulation signals as described herein. An implantation process, along with an explantation process, will be described in more detail with respect to FIG. 4. Electrode 103, as described above, may be configured to deliver stimulation signals generated by pulse generator 320 to target nerve tissue 322. The stimulation signals may be carried to electrode 103 of stim end 315 for delivery to target nerve tissue 322 by a cable disposed within the lead body of stimulation lead 100 from pulse generator 320 via contact 203 of term end 310.

In embodiments, term end 310 of stimulation lead 100 may be electrically coupled to pulse generator 320. Term end 310 may be configured and may include the same components as the term end of stimulation lead 100 described with respect to FIG. 2A. In particular, term end 310 may include contact 203 configured to receive stimulation signals from pulse generator 320 and transmit, via the cable disposed within the lead body of stimulation signal 100, those stimulation signals to stim end 315.

In embodiments, pulse generator 320, also referred to herein as a stimulation signal generator, may be implemented by circuitry, processor-based device, or software, and may be configured to generate electrical stimulation pulses. The pulse generating circuitry may be coupled to stimulation lead 100 through an electrical connection provided in a terminal of pulse generator 320. In embodiments, contact 203 of term end 310 may be configured to electrically connect to the terminal of pulse generator 320. In this manner, stimulation signals are carried from pulse generator 320 to electrode 103 for delivery to target nerve tissue 322.

In some embodiments, pulse generator 320 may comprise an external device that is not implanted within a patient. In aspects, the external device may be a wearable device, or may be a desktop device. In some embodiments, pulse generator 320 may comprise an implantable pulse generator (IPG) that is adapted to generate electrical pulses for application to the target nerve tissue. In embodiments, pulse generator 320 may include a controller, pulse generating circuitry, a battery, far-field and/or near field communication circuitry (e.g., BLUETOOTH communication circuitry, and/or Wi-Fi communication circuitry), and/or other appropriate circuitry and components of the device. The controller may be include a microcontroller or other suitable processor for controlling the various other components of the pulse generator. Software code may be stored in memory of pulse generator 320 for execution by the microcontroller or processor to control the various components of pulse generator 320.

During operation of system 300, pulse generator 320 may generate at least one stimulation signal. The at least one stimulation signal may be provided to stimulation lead 100, via contact 203 of term end 310, which may be electrically connected to pulse generator 320. For example, contact 203 may be connected (e.g., via physical contact) to a terminal of pulse generator 320. The at least one stimulation signal may be carried, via a cable disposed within the lead body of stimulation lead 100, to stim end 315. Specifically, the at least one stimulation signal may be passed from the cable to a proximal metal ferrule electrically coupled to the cable and to electrode 103, and then from the proximal metal ferrule to electrode 103. The at least one stimulation signal is then delivered to target nerve tissue 322 from electro 103. In embodiments, the same process may be repeated many times to deliver multiple stimulation signals to target nerve tissue 322, depending on the type of stimulation treatment being delivered to the patient.

It is noted that although a single stimulation lead is illustrated in the examples described herein, this is merely by way of example and not intended to be limiting in any way. As such, it should be understood that multiple stimulation leads, configured in accordance with aspects of the present disclosure, may be used to implement the stimulation systems described herein and to provide stimulation treatments using stimulation signals.

Figure 4:
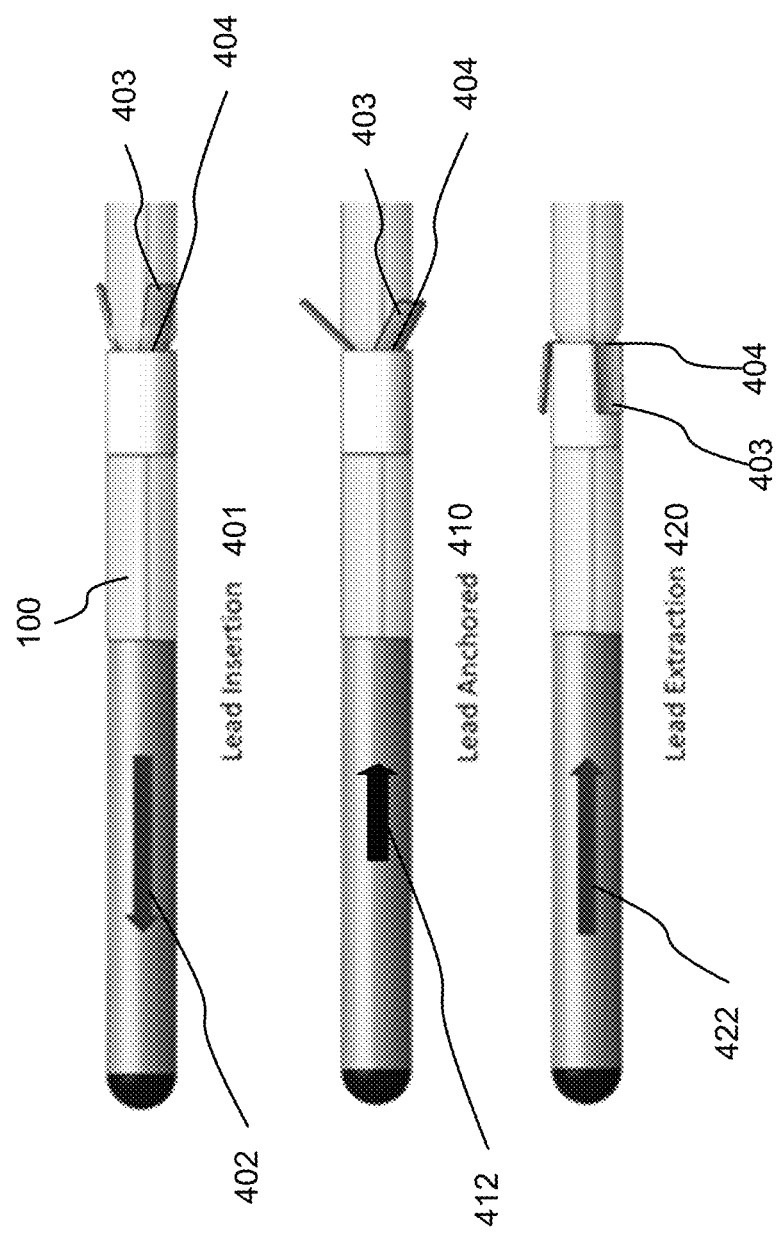
FIG. 4 shows a diagram illustrating processes for insertion, anchoring, and extraction of a stimulation lead implemented in accordance with aspects of the present disclosure.

FIG. 4 shows a diagram illustrating processes for insertion, anchoring, and extraction of a stimulation lead implemented in accordance with aspects of the present disclosure. In particular, FIG. 4 illustrates the functionality of a tine component of a stimulation lead during operation and use of the stimulation lead. FIG. 4 shows stimulation lead 100 configured in accordance with the present disclosure. For example, stimulation lead may include a stim end configured for implantation into a patient and configured to deliver stimulation signals to a target nerve tissue. As illustrated in FIG. 4, the stim end of stimulation lead 100 may include a tine component. The tine component of stimulation lead 100 may be tine component 105 described with respect to FIG. 1A. The tine component may be configured to provide a retaining force against a force exerted in the extraction direction upon the stimulation lead, while allowing insertion of the stim end of the stimulation lead during implantation, and extraction of the stim end during explantation. The tine component may include a plurality of tines 403. As described above, tines 403 may be folded at folding point 404 at an anchoring angle which positions tines 403 to point away from the stim end of stimulation lead 100.

During stim end insertion, as shown in 401, a insertion force 402 may be applied on the stimulation lead 100. The insertion force may act to push the stim end of stimulation lead 100 into the implantation area (not shown). As the stim end of the stimulation lead 100 is inserted into and enters the implantation area within the patient, tines 403 may come into contact with the patient's tissue at the site of implantation. As insertion force 402 continues to be applied in the direction of the stim end, the patient's tissue may create an opposing force against tines 403. In embodiments, tines 403 may be configured such that tines 403 may fold down onto the lead body of stimulation lead 100 in response to the opposing force acting upon tines 403. In this case, folding point may yield and allow tines 403 to fold down, thereby allowing the stim end of stimulation lead 100 to be inserted into the implantation area.

In aspects, once the stem end having tines 403 thereon has been inserted into the implantation area, tines 403 may again fold up into the anchoring position as illustrated in 410. In aspects, the folding up may be due to a material memory which may bias the tines 403 toward the anchoring position and may cause tines 403 to return to the anchoring angle once a force acting upon tines 403 has been removed. As shown in 410, tines 403 may remain in the anchoring position in which tines 403 are folded at folding point 404 at an anchoring angle which positions tines 403 to point away from the stim end of stimulation lead 100.

In the example illustrated in FIG. 4, a force 412 exerted in the extraction direction may be applied against stimulation lead 100. In embodiments, force 412 may be a pulling force due to normal use (e.g., due to patient's normal movement) that causes stimulation lead 100 to pull away from the implantation area. Thus, force 412 may not be intended to extract stimulation lead 100 from the patient. In this example, force 412 may not exceed a predetermined threshold. As such, it may not be desired that stimulation lead 100 be removed or extracted from the patient, or that displacement of stimulation lead 100 occurs within the implantation area due to force 412. In this example, the pulling action of force 412 may cause tines 403 to push against the patient's tissue at the implantation area causing a resistance to movement due to force 412. For example, the anchoring angle of tines 403 may cause a retaining force that prevents tines 403 from folding at folding point 404, as extraction force 412 does not exceed the threshold and is thus not sufficient to overcome the retaining force and cause tines 403 to fold up. In this case, tines 403 remain at the anchoring angle, thereby preventing displacement and/or extraction of stimulation lead 100 within/from the implantation area.

However, as shown at 420, extraction force 422 may be applied against stimulation lead 100, and extraction force 422 may be sufficient to cause tines 403 to fold up at folding point 404. As shown at 420, extraction force 422 may exceed the predetermined threshold, and thus, it may be determined to be an explantation force intending to remove the stim end of stimulation lead from within the patient, rather than simply being normal use pulling. In this case, the extraction force is sufficient to overcome the retaining force. As such, as stimulation lead 100 is pulled away from the implantation area with extraction force 422, tines 403 may press against the patient's tissue at the implantation are, which may cause tines 403 to fold up, and then down onto the lead body of stimulation lead 100 in the direction of the distal end of stimulation lead 100, thereby allowing stimulation lead 100 to be extracted from the implantation area.

Figure 5:
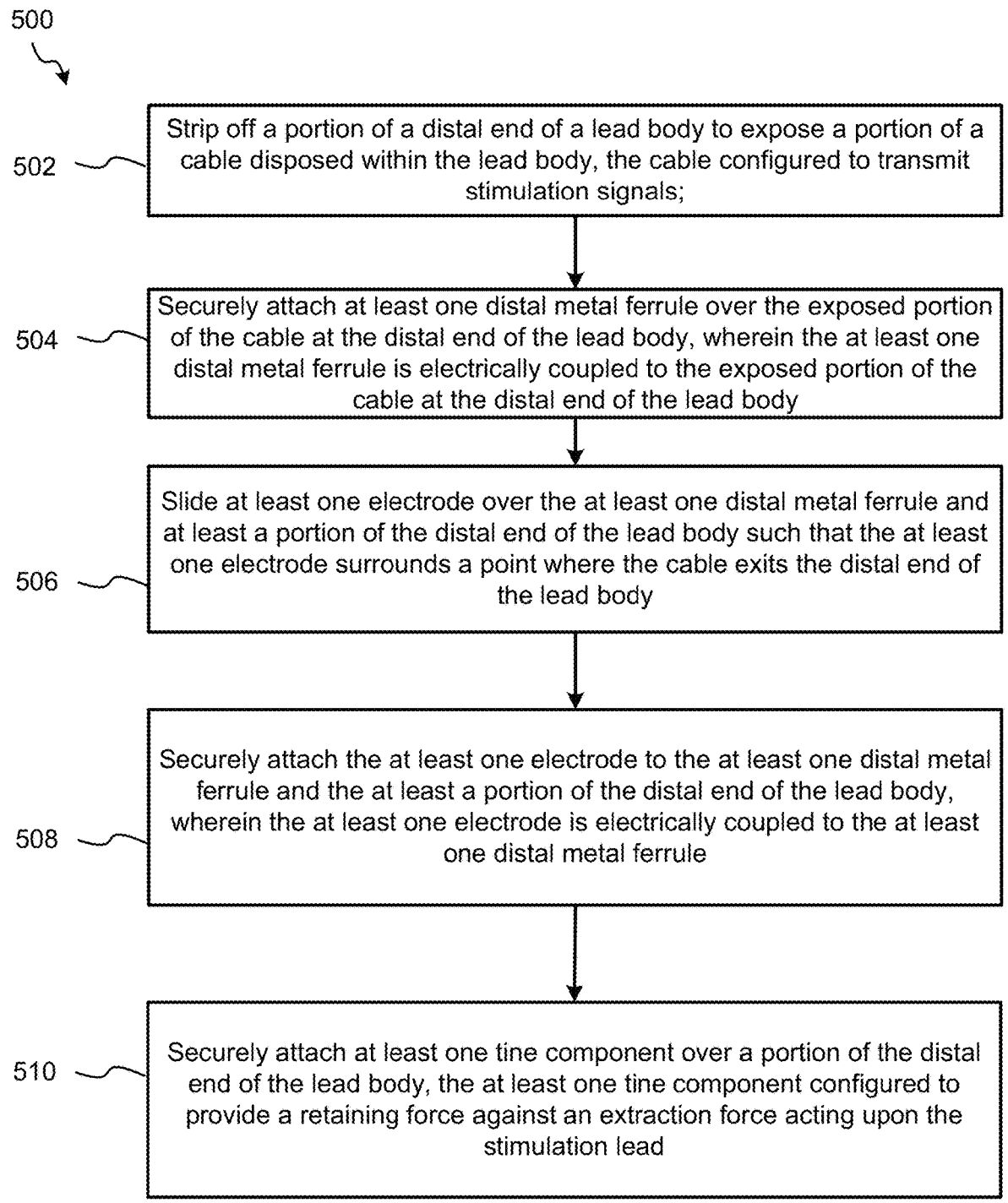
FIG. 5 is a flow diagram illustrating an example process for manufacturing a stimulation lead in accordance with aspects of the present disclosure.
Figure 6A:
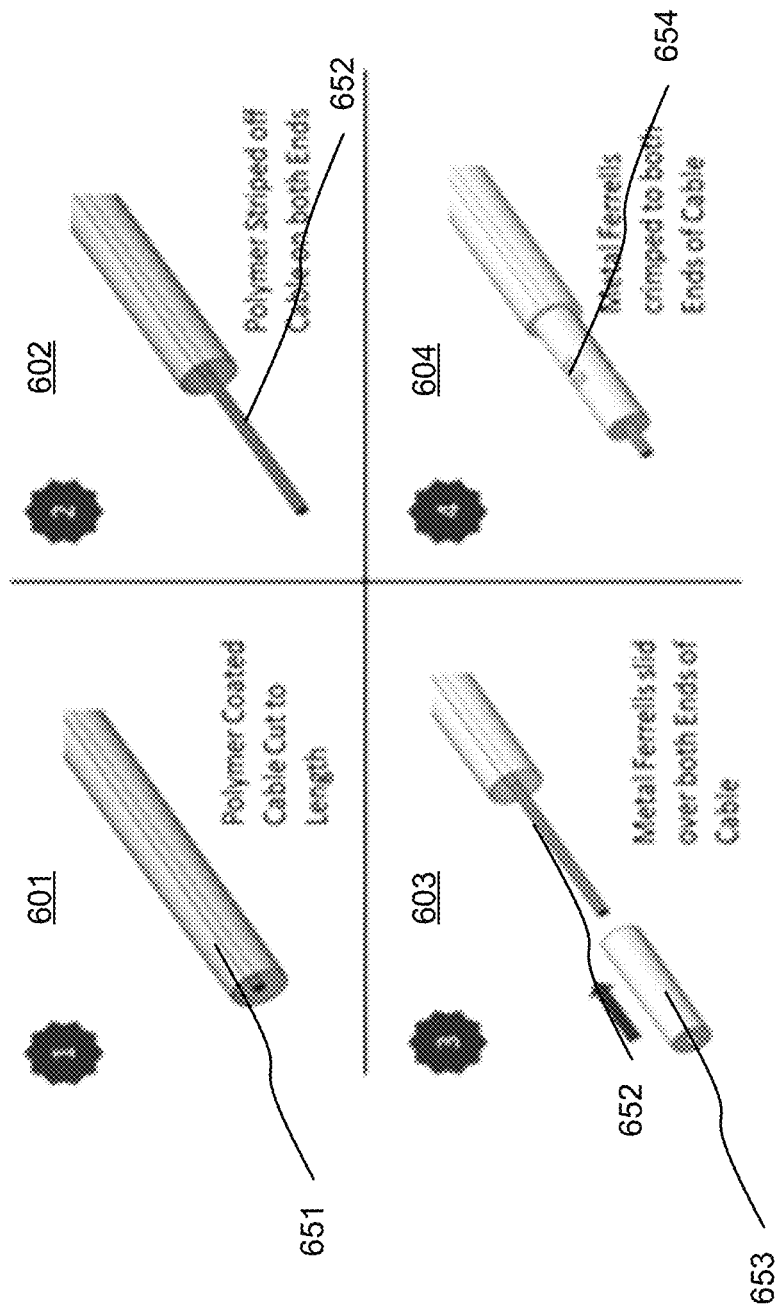
FIGS. 6A-6B show a diagram illustrating an example process for manufacturing a stimulation lead in accordance with aspects of the present disclosure.
Figure 6B:
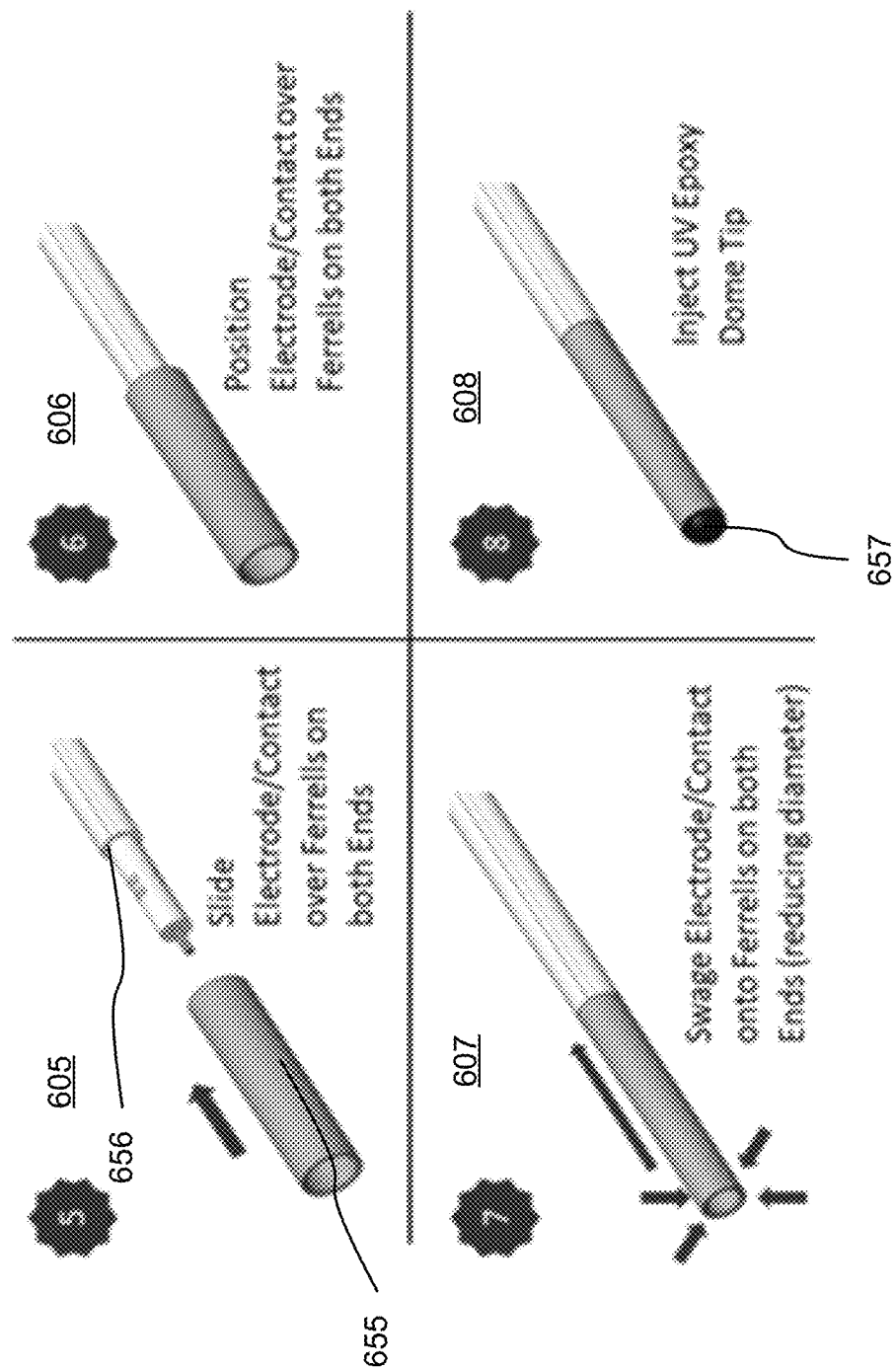
Figure 6C:
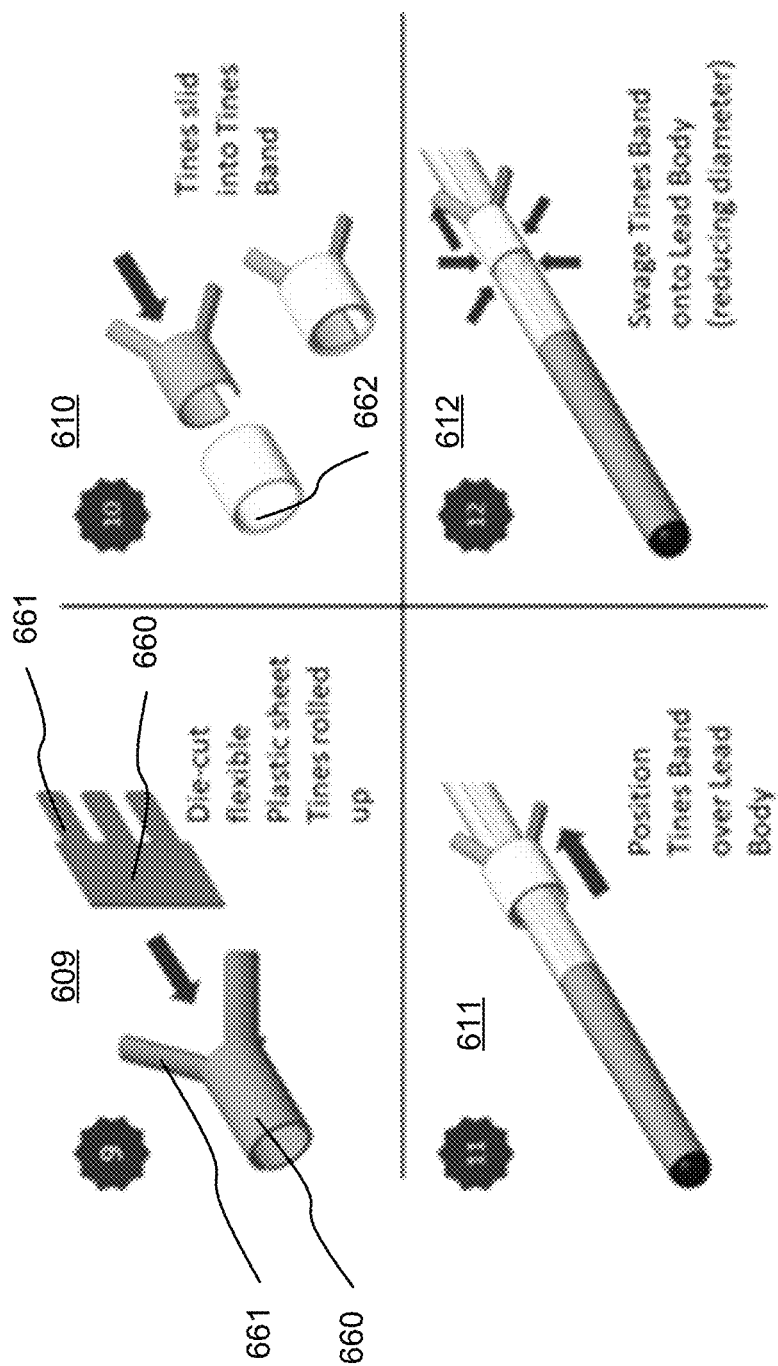
FIG. 6C shows a diagram illustrating an example process for manufacturing a tine component in accordance with aspects of the present disclosure.

FIG. 5 is a flow diagram illustrating an example process 500 for manufacturing a stimulation lead in accordance with aspects of the present disclosure. The steps of process 500 will be discussed herein also with respect to the illustrative example of FIGS. 6A-6C. FIGS. 6A-6C show a diagram illustrating an example process for manufacturing a stimulation lead in accordance with aspects of the present disclosure. In embodiments, the stimulation lead described with respect to FIGS. 5 and 6A-6C may be stimulation lead 100 described above with respect to FIGS. 1A-1B, 2A-2B, 3, and 4, including the individual components described therein.

At block 502, a portion of a distal end of a lead body of a stimulation lead may be stripped off to expose a portion of a cable disposed within the lead body (e.g., such as within a lumen defined longitudinally within the lead body). In embodiments, the cable disposed within the lead body may be configured to transmit stimulation signals. In embodiments, the cable may comprise one or more conductors, and may be made of a conductive material. As illustrated in step 601 of FIG. 6A, lead body 651 made of a polymer and including a cable disposed within maybe cut to length. At step 602, lead body 651 is stripped off to expose cable portion 652, disposed within lead body 651.

At block 504, at least one distal metal ferrule may be securely attached onto the exposed portion of the cable at the distal end of the lead body. In embodiments, securely attaching the metal ferrule onto the exposed portion of the cable may include sliding the at least one distal metal ferule over the exposed portion of the cable, and crimping the at least one distal metal ferrule onto the exposed portion of the cable. In embodiments, the distal metal ferrule may be constructed of a conductive material, and crimping the distal metal ferrule onto the exposed portion of the cable may electrically couple the at least one distal metal ferrule to the exposed portion of the cable at the distal end of the lead body. As illustrated in step 603 of FIG. 6A, metal ferrule 653 may be positioned over exposed cable portion 652. At step 604, metal ferrule 653 may be crimped onto cable portion 652. For example, metal ferrule 653 may be crimped onto cable portion 652 at point 654, to securely attach metal ferrule 653 to cable portion 652.

At block 506, an electrode is positioned over the at least one distal metal ferrule and at least a portion of the distal end of the lead body such that the electrode covers a transition point where the cable exits the distal end of the lead body, and at block 508, the electrode is securely attached to the at least one distal metal ferule and the at least a portion of the distal end of the lead body. For example, as shown in steps 605-607 of FIG. 6B, electrode 655 may be positioned e.g., by sliding, over cable portion 652, metal ferrule 653, transition point 656, and may also cover a further portion of the lead body 651. At 607, electrode 655 is securely attached (e.g., by swaging to reduce the diameter of electrode 655) onto the stimulation lead. As such, electrode 655 provides a resisting force against a bending force acting upon transition point 656, which is the point at which stimulation lead transitions from lead body 651 to exposed cable portion 652, and is a particularly vulnerable point for mechanical failure.

In addition, electrode 655 may be constructed of a conductive material, and may be electrically connected (e.g., via the physical contact caused by the swaging) to metal ferrule 653. As such, electrode 655 may be configured to receive stimulation signals from a stimulation signal generator, via cable 652 and metal ferrule 653, and to deliver the stimulation to target nerve tissue.

At block 510 at least one tine component is securely attached to a portion of the distal end of the lead body. In aspects, the at least one tine component may be configured to provide a retaining force against a force in the extraction direction acting upon the stimulation lead, while allowing insertion of the stimulation lead during implantation, and extraction of the stimulation lead during explantation. A process for manufacturing the at least one tine component will be discussed below with respect to FIG. 6C.

In some embodiments, as illustrated in step 608 of FIG. 6B, a UV epoxy dome 657 may be injected at a tip of the distal end of the lead body thereby covering the end of electrode 655. In embodiments, UV epoxy dome 657 may also cover and/or protect the end portion of cable 652 and metal ferrule 653.

It is noted that the same process described above may be used to manufacture the proximal end, or term end, of the stimulation lead of embodiments, with some modifications. For example, a tine component may not be attached to the proximal end of the stimulation lead, as the proximal end is not configured for implantation, but rather may be configured to connect to a stimulation signal generator. Additionally or alternatively, instead of an electrode, the proximal end may include a contact. However, in some embodiments, the electrode and the contact may be the same type of component and in that case the difference is merely semantic.

FIG. 6C shows a diagram illustrating an example process for manufacturing a tine component in accordance with aspects of the present disclosure. As noted above, the tine component may be configured to be attached to the distal end, or stim end, of a stimulation lead and may be configured to provide a retaining force against a force in the extraction direction acting upon the stimulation lead, while allowing insertion of the stimulation lead during implantation, and extraction of the stimulation lead during explantation, as described above with respect to FIG. 4.

At step 609, a tine sheet may be rolled into a cylindrical shape such that a band portion forms a cylindrical band with tine features disposed around the band portion. In aspects, the tine sheet may be fabricated (e.g., die-cut, formed, 3D printed, mold injected, etc.) from a highly flexible polymer sheet. In embodiments, the tine sheet may include band portion 660 and a plurality of tine features 661 disposed around the band portion. In embodiments, each tine feature of the plurality of tine features 661 may be deflected or bent into an anchoring angle at a hinge point. The tine sheet may then be treated with heat, chemicals, or any other method or substance, to cause the tine sheet material to develop a material memory biasing the plurality of tines toward the anchor position, such that when the tines are deflected, the tines tend to spring back to the anchor position.

At step 610, the rolled up tine sheet is inserted into band 662. At step 611, band 662 and the rolled up tine sheet are positioned (e.g., slid) over the lead body of the stimulation lead (e.g., at a position proximate to the electrode), and at step 612, band 662 is securely attached to the lead body. In aspects, securely attaching band 662 to the lead body may include swaging band 662 to reduce its diameter, or may include crimping band 662 onto the lead body of the stimulation lead.

It is noted that the scope of the present application is not intended to be limited to the particular embodiments of the process, machine, manufacture, composition of matter, means, methods and steps described in the specification.

While this specification contains many implementation details, these should not be construed as limitations on the scope of the invention or of what may be claimed, but rather as descriptions of features specific to particular implementations of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking may be advantageous.

Thus, particular implementations of the invention have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

Although the embodiments of the present disclosure and their advantages have been described in detail, it should be understood that various changes, substitutions and alterations can be made herein without departing from the spirit and scope of the disclosure as defined by the appended claims. Moreover, the scope of the present disclosure is not intended to be limited to the particular embodiments of the process, machine, manufacture, composition of matter, means, methods and steps described herein. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A stimulation lead comprising:
   a lead body having a distal end and a proximal end;
   a cable disposed within at least a portion of the lead body, the cable configured to transmit stimulation signals, wherein a distal portion of the cable extends out of the distal end of the lead body;
   at least one distal ferrule disposed around the distal portion of the cable that extends out of the distal end of the lead body, wherein the at least one distal ferrule is securely attached to the distal portion of the cable, and wherein the at least one distal ferrule is electrically coupled to the distal portion of the cable;
   at least one electrode disposed around the at least one distal ferrule and at least a portion of the distal end of the lead body such that the at least one electrode surrounds a point where the cable exits the distal end of the lead body, wherein the at least one electrode is securely attached to the at least one distal ferrule and the at least a portion of the distal end of the lead body, and wherein the at least one electrode is electrically coupled to the at least one distal ferrule; and at least one tine component disposed around a portion of the distal end of the lead body, the at least one tine component configured to provide a retaining force against a force in a direction of extraction acting upon the stimulation lead, and wherein at least one tine component is securely attached to the portion of the distal end of the lead body.

2. The stimulation lead of claim 1, wherein a proximal portion of the cable extends out of the proximal end of the lead body, and further comprising:

at least one proximal ferrule disposed around the proximal portion of the cable that extends out of the proximal end of the lead body, wherein the at least one proximal ferrule is crimped onto the proximal portion of the cable, and wherein the at least one proximal ferrule is electrically coupled to the proximal portion of the cable; and at least one contact disposed around the at least one proximal ferrule and at least a portion of the proximal end of the lead body such that the at least one contact surrounds a point where the cable exits the proximal end of the lead body, wherein the at least one contact is swaged onto the at least one proximal ferrule and the at least a portion of the proximal end of the lead body.

3. The stimulation lead of claim 1, wherein the proximal end of the lead body is configured to connect to a stimulation generator.

4. The stimulation lead of claim 1, wherein the distal end of the lead body is configured to be implanted into a patient to deliver stimulation pulses.

5. The stimulation lead of claim 1, wherein the at least one tine component includes a plurality of tine features configured to provide the retaining force against the force in the direction of extraction acting upon the stimulation lead.

6. The stimulation lead of claim 5, wherein each of the plurality of tine features are disposed around the at least one tine component and are folded at a folding point such that each of the plurality of tine features is angled toward to proximal end of the lead body.

7. The stimulation lead of claim 6, wherein the plurality of tine features are configured to fold down at the folding point toward the lead body during insertion of the stimulation lead.

8. The stimulation lead of claim 6, wherein the plurality of tine features are configured to resist folding up toward the distal end of the lead body when the force in the direction of extraction is applied on the stimulation lead thereby preventing extraction of the stimulation lead.

9. The stimulation lead of claim 7, wherein the plurality of tine features are configured to fold up toward the distal end of the lead body when the force in the direction of extraction applied on the stimulation lead exceeds a threshold thereby allowing extraction of the stimulation lead.

10. The stimulation lead of claim 1, wherein the lead body is made of an insulative material, and the cable is made of a conductive material.

11. The stimulation lead of claim 1, further comprising: an epoxy dome disposed at a tip of the distal end of the lead body, the epoxy dome covering an end portion of the at least one electrode and an end portion of the cable.

12. The stimulation lead of claim 1, wherein securely attaching the at least one electrode to the at least one distal ferrule and the at least a portion of the distal end of the lead body includes swaging the at least one electrode onto the at least one distal ferrule and the at least a portion of the distal end of the lead body.

13. The stimulation lead of claim 1, wherein securely attaching the at least one distal ferrule to the distal portion of the cable includes crimping the at least one distal ferrule onto the distal portion of the cable.

14. The stimulation lead of claim 1, wherein securely attaching the at least one tine component to the portion of the distal end of the lead body includes:

inserting a band portion of the at least one tine component into a tine band;

positioning the tine band with the band portion of the at least one tine component over the portion of the distal end of the lead body; and swaging the tine band onto the portion of the distal end of the lead body thereby securely attaching the at least one tine component to the portion of the distal end of the lead body.

15. A method of manufacture of a stimulation lead comprising:

securely attaching at least one distal ferrule to an exposed portion of a cable at a distal end of a lead body having the distal end and a proximal end, the cable disposed within the lead body and configured to transmit stimulation signals, wherein the at least one distal ferrule is electrically coupled to the exposed portion of the cable at the distal end of the lead body;

positioning at least one electrode over the at least one distal ferrule and at least a portion of the distal end of the lead body such that the at least one electrode surrounds a point where the cable exits the distal end of the lead body;

securely attaching the at least one electrode to the at least one distal ferrule and the at least a portion of the distal end of the lead body, wherein the at least one electrode is electrically coupled to the at least one distal ferrule; and securely attaching at least one tine component to a portion of the distal end of the lead body, the at least one tine component configured to provide a retaining force against a force in a direction of extraction acting upon the stimulation lead.

16. The method of manufacture of claim 15, further comprising:

stripping a portion of the distal end of the lead body to expose the exposed portion of the cable disposed within the lead body.

17. The method of manufacture of claim 15, further comprising:

stripping off a portion of a proximal end of the lead body to expose another portion of the cable disposed within the lead body;

crimping at least one proximal ferrule over the exposed another portion of the cable at the proximal end of the lead body, wherein the at least one proximal ferrule is electrically coupled to the exposed another portion of the cable at the proximal end of the lead body;

sliding at least one contact over the at least one proximal ferrule and at least another portion of the proximal end of the lead body such that the at least one contact surrounds a point where the cable exits the proximal end of the lead body; and swaging the at least one contact to reduce a diameter of the at least one contact thereby securing the at least one contact to the at least one proximal ferrule and the at least another portion of the proximal end of the lead body, wherein the at least one contact is electrically coupled to the at least one proximal ferrule.

18. The method of manufacture of claim 17, further comprising configuring the proximal end of the lead body to connect to a stimulation pulse generator.

19. The method of manufacture of claim 15, further comprising:
  forming, prior to swaging the at least one tine component over the portion of the distal end of the lead body, the at least one tine component by:
    rolling a tine sheet into a cylindrical shape, the tine sheet including a band portion and a tine portion, the tine portion including a plurality of tines;
    sliding the band portion of the cylindrical shape into a tine band; and
    folding each tine of the plurality of tines to an angle configured to provide the retaining force against the force in the direction of extraction acting upon the stimulation lead; and
  sliding the at least one tine component over the portion of the distal end of the lead body, wherein swaging the tine component includes swaging the tine band onto the portion of the distal end of the lead body.

20. The method of manufacture of claim 19, wherein each of the plurality of tines is configured to fold down toward the lead body during insertion of the stimulation lead.

21. The method of manufacture of claim 19, wherein each of the plurality of tines is configured to fold up toward the distal end of the lead body when the force in the direction of extraction applied on the stimulation lead exceeds a threshold thereby allowing extraction of the stimulation lead.

22. The method of manufacture of claim 15, further comprising:
  injecting an epoxy dome at a tip of the distal end of the lead body, the epoxy dome covering an end portion of the at least one electrode and an end portion of the cable at the distal end of the lead body.

23. The method of manufacture of claim 15, wherein securely attaching the at least one electrode to the at least one distal ferrule and the at least a portion of the distal end of the lead body includes swaging the at least one electrode to reduce a diameter of the at least one electrode thereby securing the at least one electrode onto the at least one distal ferrule and the at least a portion of the distal end of the lead body.

24. The method of manufacture of claim 15, wherein securely attaching the at least one distal ferrule to the distal portion of the cable includes crimping the at least one distal ferrule onto the distal portion of the cable.

25. The method of manufacture of claim 15, wherein securely attaching the at least one tine component to the portion of the distal end of the lead body includes:
  inserting a band portion of the at least one tine component into a tine band;
  positioning the tine band with the band portion of the at least one tine component over the portion of the distal end of the lead body; and
  swaging the tine band onto the portion of the distal end of the lead body thereby securely attaching the at least one tine component to the portion of the distal end of the lead body.

26. A method of providing stimulation using a stimulation lead, the method comprising:
  implanting a distal end of the stimulation lead within a patient such that at least one electrode of the stimulation lead is disposed adjacent to tissue, wherein the stimulation lead includes:
    a cable disposed within at least a portion of a lead body of the stimulation lead and configured to transmit stimulation signals;
    at least one distal metal ferrule crimped around a distal portion of the cable that extends out of the distal end of the lead body, wherein the at least one distal metal ferrule is electrically coupled to the distal portion of the cable;
    the at least one electrode swaged around the at least one distal metal ferrule and at least a portion of the distal end of the lead body such that the at least one electrode surrounds a point where the cable exits the distal end of the lead body, wherein the at least one electrode is electrically coupled to the at least one distal metal ferrule; and
    at least one tine component swaged around a portion of the distal end of the lead body, the at least one tine component configured to provide a retaining force against a force in a direction of extraction acting upon the stimulation lead;
  connecting a proximal end of the stimulation lead to a stimulation signal generator; and
  activating the stimulation signal generator to deliver the stimulation signals to the at least one electrode adjacent to the tissue thereby providing stimulation to the patient.

27. The method of claim 26, wherein the stimulation lead further includes the proximal end of the stimulation lead includes:
  a proximal portion of the cable that extends out of the proximal end of the lead body, and further comprising:
  at least one proximal metal ferrule crimped around a proximal portion of the cable that extends out of the proximal end of the lead body, wherein the at least one proximal metal ferrule is electrically coupled to the proximal portion of the cable; and
  at least one contact swaged around the at least one proximal metal ferrule and at least a portion of the proximal end of the lead body such that the at least one contact surrounds a point where the cable exits the proximal end of the lead body, wherein the at least one contact is electrically coupled to the at least one proximal metal ferrule.

28. The method of claim 26, wherein implanting the distal end of the stimulation lead within the patient incudes:
  positioning the distal end of the stimulation lead on a location within the patient where the distal end of the stimulation is to be implanted;
  applying an insertion force against the distal end of the stimulation lead, wherein applying the insertion force causes a plurality of tine features of the at least one tine component to fold down onto the lead body and away from the distal end of the stimulation lead thereby allowing insertion of the distal end of the stimulation lead onto the patient.

29. The method of claim 26, further comprising extracting the distal end of the stimulation lead from the patient, wherein extracting the distal end of the stimulation lead from the patient includes:
  applying the force in the direction of extraction against the stimulation lead, wherein applying the force in the direction of extraction:

causes, when the force in the direction of extraction exceeds a threshold, a plurality of tine features of the at least one tine component to fold up onto the lead body and toward the distal end of the stimulation lead thereby allowing extraction of the stimulation lead from the patient; and causes, when the force in the direction of extraction does not exceed the threshold, the plurality of tine features of the at least one tine component to resist folding up onto the lead body and toward the distal end of the stimulation lead thereby preventing extraction of the stimulation lead from the patient until the extraction force exceeds the threshold.

\* \* \* \* \*